United States Patent [19]

Bergthaller et al.

[11] Patent Number: 5,683,863
[45] Date of Patent: Nov. 4, 1997

[54] PHOTOGRAPHIC SILVER HALIDE MATERIAL

[75] Inventors: Peter Bergthaller, Bergisch Gladbach; Hans-Ulrich Borst, Elsdorf; Peter Bell, Köln; Ralf Büscher, Lohmar; Johannes Willsau, Leverkusen; Thomas Stetzer, Langenfeld, all of Germany

[73] Assignee: AGFA-Gevaert-AG, Leverkusen, Germany

[21] Appl. No.: 571,408

[22] Filed: Dec. 13, 1995

[30] Foreign Application Priority Data

Dec. 22, 1994 [DE] Germany .................. 44 45 966.1

[51] Int. Cl.$^6$ ................................. G03C 1/09
[52] U.S. Cl. .................. 430/613; 430/567; 430/600; 430/607
[58] Field of Search ................ 430/600, 613, 430/567, 607

[56] References Cited

U.S. PATENT DOCUMENTS 2,278,947   4/1942   Riester .................. 430/600
5,238,807   8/1993   Sasaki et al. .......... 430/600

*Primary Examiner*—Thorl Chea
*Attorney, Agent, or Firm*—Connolly & Hutz

[57] ABSTRACT

A color photographic silver halide material having at least one silver halide emulsion layer, which is stabilized with a compound of formula (I) or (II)

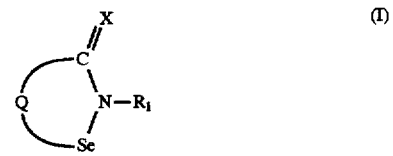

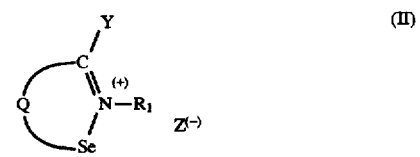

where

X represents O or $NR_2$

Y represents halogen, $Z^{\ominus}$ represents an anion, $R_1$ represents hydrogen or a substituent, or jointly with X represents the remaining members of a condensed ring $R_2$ represents hydrogen or a substituent, and Q represents the atoms required for the completion of a 5- or 6-membered ring, is characterized by enhanced stability.

13 Claims, No Drawings

PHOTOGRAPHIC SILVER HALIDE MATERIAL

This invention relates to a photographic silver halide material having at least one silver halide emulsion layer, the silver halide emulsion of which contains a new stabiliser.

Silver halide emulsions are usually protected from variations in their properties by the addition of suitable stabilisers. In particular, stabilisation is required of the sensitivity both in the unexposed and in the exposed states (latent image stability), the most important destabilising influences being temperature and moisture. Both unexposed silver halide material and silver halide material which has been exposed but which has not yet been processed are always subjected to these influences.

Known latent image stabilisers such as thiazolidine-4-carboxylic acid of formula

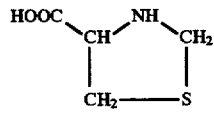 (A)

have an inadequate effect, particularly under tropical storage conditions.

The object of the invention was the provision of new stabilisers, which protect both unexposed and exposed photographic silver halide material from a drop in sensitivity, particularly under tropical storage conditions.

It has now been found that this object is achieved with isoselenazolones.

The present invention therefore relates to a photographic silver halide material of the type cited at the outset, in which at least one silver halide emulsion is stabilised with a compound of formulae (I) or (II):

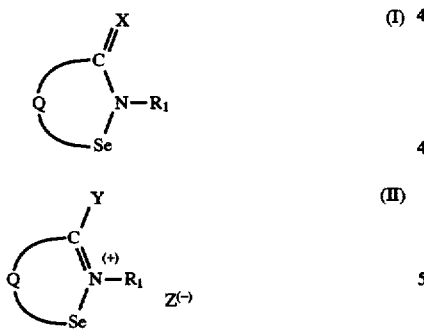

where

X represents O or NR$_2$,

Y represents halogen, particularly chlorine,

Z$^{\ominus}$ represents an anion, particularly chloride,

R$_1$ represents hydrogen or a substituent, or jointly with X represents the remaining members of a condensed ring R$_2$ represents hydrogen or a substituent, and Q represents the atoms required for the completion of a 5- or 6-membered ring.

The R$_1$ and R$_2$ substituents comprise alkyl, aryl, acyl and heterocyclic groups in particular, which may themselves be substituted further.

Preferred stabilisers correspond to formula (III):

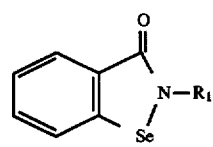 (III)

where R$_1$ has the meaning given above.

Suitable compounds of formula (III) are:

| Compound | R$_1$ |
|---|---|
| 1 | phenyl |
| 2 | benzyl |
| 3 | cyclohexyl |
| 4 | 2-fluorophenyl |
| 5 | 4-carboxyphenyl |
| 6 | 4-trifluoromethylphenyl |
| 7 | 4-(1-carboxyethyl)-phenyl |
| 8 | 4-dimethylaminophenyl |
| 9 | pyrimidinyl-(2) |
| 10 | 3-hydroxypyridinyl-(2) |
| 11 | 3,3-dioxo-3-thiacyclopentyl |
| 12 | tert.-butyl |
| 13 | ω-carboxy-n-pentyl |
| 14 | benzthiazolyl-(2) |
| 15 | acetyl |
| 16 | 2-pyridyl-(4-)-ethyl hydrochloride |
| 17 | 2,2-dimethoxyethyl |
| 18 | hydrogen |

Other suitable compounds of formulae (I), (II) and (III) are:

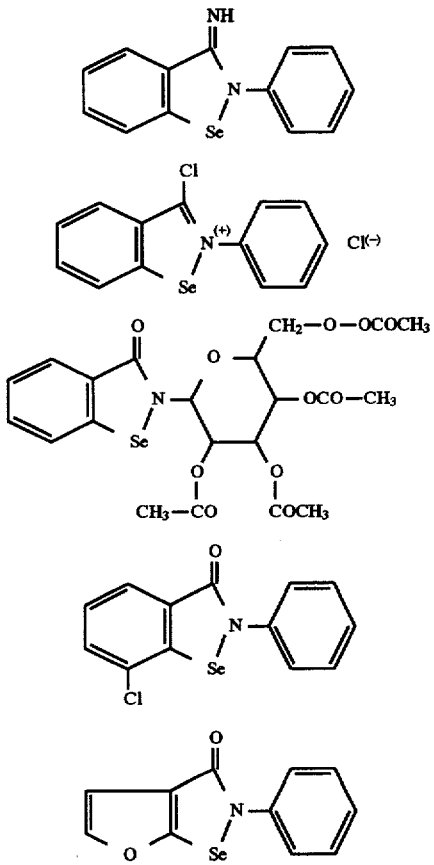

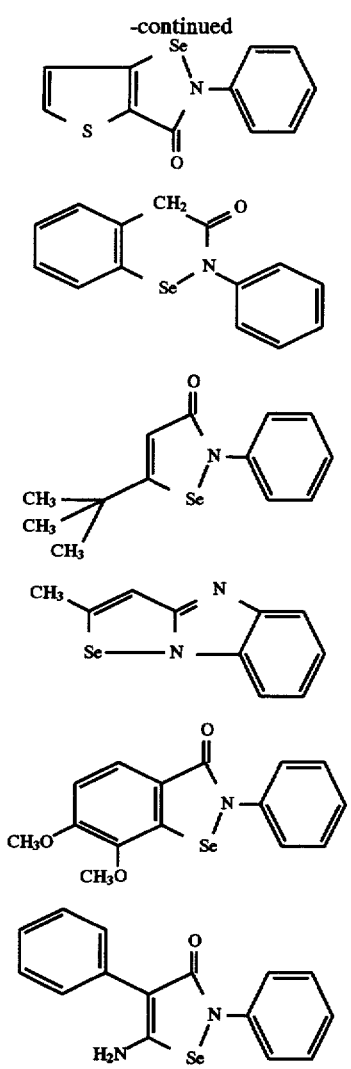
-continued

Accurate information on the preparation of benzisoselenazolones is to be found in the article by Dallacker F., Peisker A., Chem. Zeitung 115 [1991], 135–39, where reference is made in particular to the possibility of subsequently alkylating unsubstituted benzisoselenazolone at the N atom.

An advantageous synthesis for N-acylated benzisoselenazolones is also described in DE-S 3 827 093.

The preparation of compound 1 is explicitly described by L. Engmann and A. Hallberg in J. Org. Chem. 54 [1989], pages 2964–2966.

Compounds of formulae (I) to (III) are added to the silver halide emulsion to be stabilised in an amount of $10^{-7}$ to $10^{-3}$ moles/mole silver halide in particular.

In addition, a customary stabilisation may be effected with sulphur-containing amino acids, for example acetyl cysteine or with compound A, these compounds being used in an amount of $10^{-7}$ to $10^{-3}$ moles/mole silver halide. The sulphur is divalent here.

The addition is preferably made after chemical ripening and spectral sensitisation.

The stabilisers according to the invention are suitable for all photographic silver halide emulsions, but are particularly suitable for colour photographic silver halide materials, preferably for colour negative and colour reversal films, the silver halide emulsions of which substantially comprise silver bromide-iodide or silver bromide-chloride-iodide emulsion with up to 15 mole % silver iodide and up to 30 mole % silver chloride, but are also suitable for colour negative and colour reversal papers, the silver halide emulsions of which are iodide-free and consist of at least 95 mole % AgCl.

Other suitable emulsions include silver chloride emulsions with up to 20 mole % AgBr and/or up to 10 mole % AgI.

Particularly preferred silver halide emulsions contain tabular grains which make up at least 50%, preferably 70% of the projected area of the emulsion and have an aspect ratio of at least 3:1, particularly 5:1 to 25:1. Their thickness is preferably less than 0.3 μm, particularly 0.03 to 0.2 μm.

The photographic materials can be developed with the usual colour developer substances, e.g. N,N-dimethyl-p-phenylenediamine, 4-amino-3-methyl-N-ethyl-N-methoxyethylaniline, 2-amino-5-diethylaminotoluene, N-butyl-N-ω-sulphobutyl-p-phenylenediamine, 2-amino-5-(N-ethyl-N-β-methanesulphonamide-ethylamino)-toluene, N-ethyl-N-β-hydroxyethyl-p-phenylenediamine, N,N-bis-(β-hydroxyethyl)-p-phenylenediamine, or 2-amino-5-(N-ethyl-N-β-hydroxyethylamino)-toluene. Other colour developers which can be used are described in J. Amer. Chem. Soc. 73, 3100 (1951), for example.

The photographic material may contain the usual colour couplers, which may be incorporated in the silver halide layers themselves. Reference is made to the publication "Colour couplers" by W. PELZ in "Mitteilungen aus den Forschungslaboratorien der Agfa, Leverkusen/Müchen" [Communications from the Agfa Research Laboratories, Leverkusen/Munich], Volume III (1961) and to K. VENKATARAMAN in "The Chemistry of Synthetic Dyes", Vol. 4, 341 to 387, Academic Press, 1971, for examples of colour couplers which may be used.

2-equivalent couplers, for example the known DIR colour couplers, may be used as additional non-diffusing colour couplers. Non-diffusing colour couplers and colour-imparting compounds may be added to the light-sensitive silver halide emulsions or to other casting solutions by the usual known methods.

Insofar as the non-diffusing colour couplers and colour-imparting compounds are compounds which are insoluble in water or alkalies, they may be emulsified in the known manner. So-called coupler solvents or oil formers are optionally used in addition for emulsifying hydrophobic compounds of this type; reference is made to U.S. Pat. Nos. 2,322,027, 2,533,514, 3,689,271, 3,764,336 and 3,765,897 for examples of these.

Gelatine is preferably used as a binder for the photographic layers. This may be completely or partially replaced by other natural or synthetic binders, however.

The emulsions may also be sensitised chemically, e.g. by the addition of sulphur-containing compounds during chemical ripening, for example allyl isothiocyanate, allyl thiourea and sodium thiosulphate. Other substances which may also be used as chemical sensitisers include reducing agents, e.g. the tin compounds described in Belgian Patent Specifications 493 464 or 568 697, and also polyamines such as diethylenetriamine or aminomethylsulphinic acid derivatives, e.g. those according to Belgian Patent Specification 547 323, or selenium compounds capable of releasing selenide or selenium, e.g. selenium ureas or heterocyclic selenones, e.g. the following compounds:

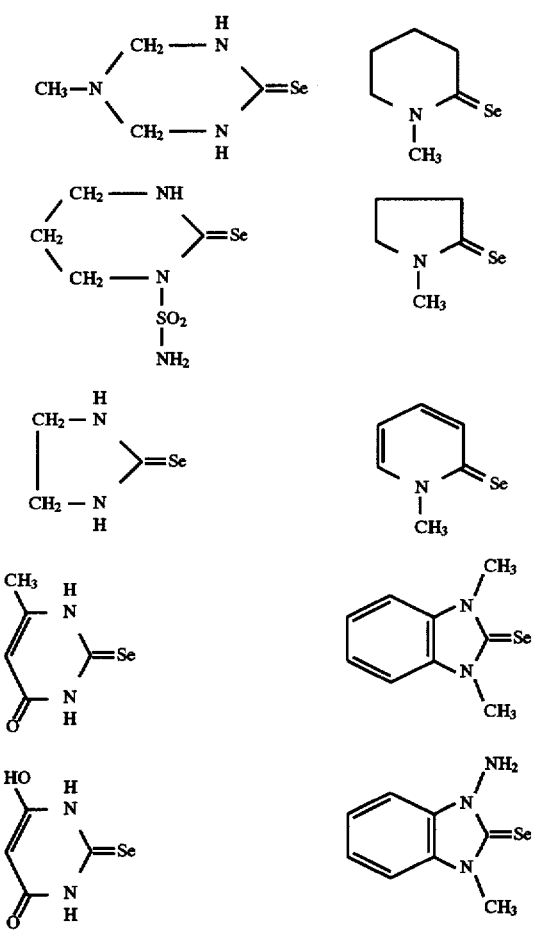

Noble metals or noble metal compounds such as gold, platinum, palladium, iridium, ruthenium or rhodium are also suitable as chemical sensitisers. It is also possible to sensitise the emulsions with polyalkylene oxide derivatives, e.g. with polyethylene oxide with a molecular weight between 1000 and 20,000, and also with condensation products of alkylene oxides and alcohols, aliphatic carboxylic acids, aliphatic amines, aliphatic diamines and amides.

The emulsions may also be spectrally sensitised, e.g. with the usual polymethine dyes such as neutrocyanines, basic or acidic carbocyanines, rhodacyanines, hemicyanines, styryl dyes, oxonoles and the like. Sensitisers of this type are described in the work by F. M. HAMER "The Cyanine Dyes and Related Compounds" (1964).

The emulsions may also contain the usual stabilisers, e.g. covalent or salt-like compounds of mercury with aromatic or heterocyclic rings such as mercaptotriazoles, simple mercury salts, sulphonium-mercury double salts and other mercury compounds. Azaindenes, preferably tetra- or pentaazaindenes, particularly those which are substituted with hydroxyl or amino groups, are also suitable as stabilisers. Compounds of this type are described in the article by BIRR, Z. Wiss. Phot. 47 (1952), 2 to 58, for example. Other suitable stabilisers, amongst others, are heterocyclic mercapto compounds, e.g. phenyl mercaptotetrazole, quaternary benzthiazole derivatives and benzotriazole.

The layers of photographic material may be hardened in the usual manner, for example with formaldehyde or with halogen-substituted aldehydes which contain a carboxyl group, such as mucobromic acid, diketones, methanesulphonic acid esters, dialdehydes and the like. The photographic layers may also be hardened with hardeners of the epoxide type, or of the heterocyclic ethylene imine or acryloyl type. Moreover, it is also possible to harden the layers by the process according to German Offenlegungsschrift 2 218 009, in order to obtain colour photographic materials which are suitable for high temperature processing. It is also possible to harden the photographic layers or the colour photographic multilayer materials with hardeners of the diazine, triazine or 1,2-dihydroquinone series. Examples of hardeners of this type include diazine derivatives which contain alkyl or arylsulphonyl groups, derivatives of hydrogenated diazines or triazines, such as 1,3,5-hexahydrotriazine for example, fluoro-substituted diazine derivatives such as fluoropyrimidine for example, or esters of 2-substituted 1,2-dihydroquinoline or 1,2-dihydroisoquinoline-N-carboxylic acids. In addition, vinyl sulphonic acid hardeners or carbodiimide or carbamoyl hardeners may be used, such as those described, for example, in German Offenlegungsschriften 2 263 602, 2 225 230 and 1 808 685, in French Patent Specification 1 491 807, in German Patent Specification 872 153 and in German Democratic Republic Patent Specification 7218. Other hardeners which can be used are described in British Patent Specification 1 268 550, for example.

EXAMPLES

Example 1

A spectrally non-sensitized silver bromide-iodide emulsion with a content of 12 mole % AgI, which essentially consisted of tabular crystals with an average diameter of 1.2 µm and a mean aspect ratio of 1:4.5, was ripened with Na thiosulphate and gold rhodanide as far as the sensitivity optimum and mixed with 350 mg 4-hydroxy-6-methyl-1,3,3a,7-tetraazaindene per 100 g AgNO$_3$.

Samples 1 to 3 were sensitized by the addition of comparison compound A.

Sample

1: $1.6 \cdot 10^{-6}$ mole/mole AgX

2: $3.2 \cdot 10^{-6}$ mole/mole AgX

3: $6.4 \cdot 10^{-6}$ mole/mole AgX

Samples 4 to 6 contained compound 1 in the following amounts

Sample

4: $1.6 \cdot 10^{-6}$ mole/mole AgX

5: $3.2 \cdot 10^{-6}$ mole/mole AgX

6: 6.4 $10^{-6}$ mole/mole AgX

Samples 7 to 9 contained compounds 3, 12 and 18 in an amount of $3.2 \cdot 10^{-6}$ mole per mole AgX.

Samples 1 to 3 were comparisons; samples 4 to 9 were according to the invention.

The samples were cast, together with an emulsified preparation of magenta coupler M-1, on to a cellulose triacetate film of thickness 120 µm, in the following deposited amounts:

Emulsion: 4 g/m$^2$ (based on AgNO$_3$)

Coupler: 68.8 g emulsified preparation per 100 g AgNO$_3$

The samples were processed as described in Example 2.

| Sample | Storage in exposed state (see 2.1.3 for data) | | Storage in unexposed state (see 2.1.4 for data) | |
|---|---|---|---|---|
| | ΔE Change in sensitivity compared with test on fresh sample | ΔS Change in $D_{min}$ compared with test on fresh sample | ΔE Change in sensitivity compared with test on fresh sample | ΔS Change in $D_{min}$ compared with test on fresh sample |
| 1 | −1.5 | +0.12 | −2.1 | +0.16 |
| 2 | −1.2 | +0.10 | −1.6 | +0.13 |
| 3 | −1.7 | +0.16 | −2.3 | +0.18 |
| 4 | −0.8 | +0.08 | −1.4 | +0.11 |
| 5 | −0.4 | +0.06 | −1.0 | +0.09 |
| 6 | −0.5 | +0.05 | −0.9 | +0.09 |
| 7 | −0.2 | +0.02 | −1.1 | +0.13 |
| 8 | −0.8 | +0.08 | −1.2 | +0.12 |
| 9 | −1.0 | +0.11 | −1.0 | +0.14 |

E = sensitivity
S = fog

Example 2.1

A multilayer colour photographic recording material was prepared by coating a cellulose triacetate film 120 μm thick in the sequence and composition given.

The amounts are given in g/m², based on the silver nitrate used in the case of the silver halide emulsions. The emulsions are also characterised by their halide content and their mean square diameter (d). The association of a substance with a function merely serves for primary characterisation; it may also have other effects.

| Layer 1 | (irradiation protection layer) | |
|---|---|---|
| | black colloidal silver | 0.25 |
| | gelatine | 0.5 |
| Layer 2 | (low-sensitivity red-sensitised layer) | |
| | silver bromide-chloride-iodide emulsion with 4 mole % iodide and 10 mole % chloride (d = 0.5 μm) | 1.9 |
| | cyan coupler C1 | 0.6 |
| | masking coupler CY-1 | $4 \times 10^{-2}$ |
| | masking coupler CM-1 | $4 \times 10^{-2}$ |
| | DIR coupler D-1 | $10^{-2}$ |
| | gelatine | 1.6 |
| Layer 3 | (medium-sensitivity red-sensitised layer) | |
| | silver bromide iodide emulsion with 6 mole % iodide (d = 1.2 μm) | 2.0 |
| | cyan coupler C-1 | 0.4 |
| | masking coupler CM-1 | $6 \times 10^{-2}$ |
| | masking coupler CY-1 | $4 \times 10^{-2}$ |
| | DIR coupler CY-1 | $4 \times 10^{-2}$ |
| | gelatine | 1.6 |
| Layer 4 | (high-sensitivity red-sensitised layer) | |
| | silver bromide-iodide emulsion with 10 mole % iodide (d = 1.4 μm) | 1.8 |
| | cyan coupler C-2 | $8 \times 10^{-2}$ |
| | gelatine | 1.2 |
| Layer 5 | (intermediate layer) | |
| | gelatine | 1.0 |
| Layer 6 | (low-sensitivity green-sensitised layer) | |
| | silver bromide-chloride-iodide emulsion with 9 mole % I⁻ and mole % Cl⁻ (d = 0.5 μm) | 1.4 |
| | magenta coupler M-1 | 0.4 |
| | masking coupler MY-1 | $7 \times 10^{-2}$ |
| | DIR coupler D-1 | $2 \times 10^{-2}$ |
| | white coupler W-1 | $4 \times 10^{-3}$ |
| | DIR coupler D-2 | $10^{-3}$ |
| | gelatine | 1.4 |
| Layer 7 | (medium-sensitivity green-sensitised layer) | |
| | silver bromide-iodide emulsion with 4 mole % I⁻ (d = 0.8 μm) | 1.2 |
| | magenta coupler M-1 | 0.2 |
| | masking coupler MY-1 | $2 \times 10^{-2}$ |
| | DIR coupler D-1 | $10^{-2}$ |
| | white coupler W-1 | $2 \times 10^{-3}$ |
| | DIR coupler D-2 | $10^{-3}$ |
| | gelatine | 1.0 |
| Layer 8 | (high-sensitivity green-sensitised layer) | |
| | silver bromide iodide emulsion with 12 mole % I⁻ (d = 1.0 μm) | 1.2 |
| | magenta coupler M-2 | 0.2 |
| | masking coupler MY-2 | $2 \times 10^{-2}$ |
| | DIR coupler D-1 | $10^{-2}$ |
| | white coupler W-1 | $3 \times 10^{3}$ |
| | gelatine | 1.2 |
| Layer 9 | (intermediate layer) | |
| | formalin scavenger F-1 | 0.4 |
| | polyvinyl pyrrolidone | $10^{-2}$ |
| | gelatine | 0.4 |
| Layer 10 | (yellow filter layer) | |
| | colloidal silver | 0.1 |
| | white coupler W-1 | $6 \times 10^{-2}$ |
| | formalin scavenger F-1 | 0.3 |
| | gelatine | 0.4 |
| Layer 11 | (low-sensitivity blue-sensitised layer) | |
| | silver bromide-chloride-iodide emulsion with 9 mole % I⁻ and 15 mole % Cl⁻ (d = 1.0 μm) | 0.7 |
| | silver bromide-chloride-iodide emulsion with 9.5 mole % I⁻ and 10.4 mole % Cl⁻ (d = 0.5 μm) | 0.3 |
| | yellow coupler Y-1 | 1.1 |
| | DIR coupler D-1 | $4 \times 10^{-2}$ |
| | polyvinyl pyrrolidone | 0.1 |
| | gelatine | 2.0 |
| Layer 12 | (medium-sensitivity blue-sensitised layer) | |
| | silver bromide-iodide emulsion with 12 mole % I⁻ (d = 1.2 μm) | 0.3 |
| | yellow coupler Y-1 | 0.1 |
| | DIR coupler D-1 | $3 \times 10^{-3}$ |
| | gelatine | 0.4 |
| Layer 13 | (high-sensitivity blue-sensitised layer) | |
| | silver bromide-iodide emulsion with 12 mole % I⁻ (d = 1.4 μm) | 0.5 |
| | yellow coupler Y-1 | 0.1 |
| | DIR coupler D-1 | $2 \times 10^{-3}$ |
| | gelatine | 0.4 |
| Layer 14 | (protective layer) | |
| | silver bromide-micrate emulsion with 4 mole % I⁻ (d = 0.05 μm) | 0.3 |
| | UV absorber UV-1 | 0.2 |
| | UV absorber UV-2 | 0.3 |
| | gelatine | 1.4 |
| Layer 15 | (hardening layer) | |
| | surface-active agent | 0.04 |
| | hardener H-1 | 0.7 |
| | gelatine | 0.2 |

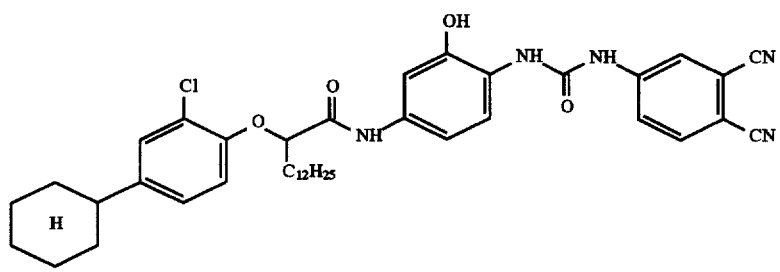
C-1
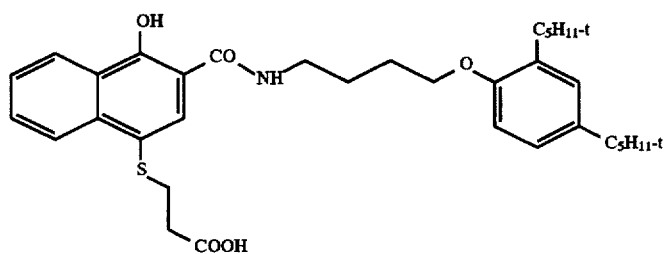
C-2
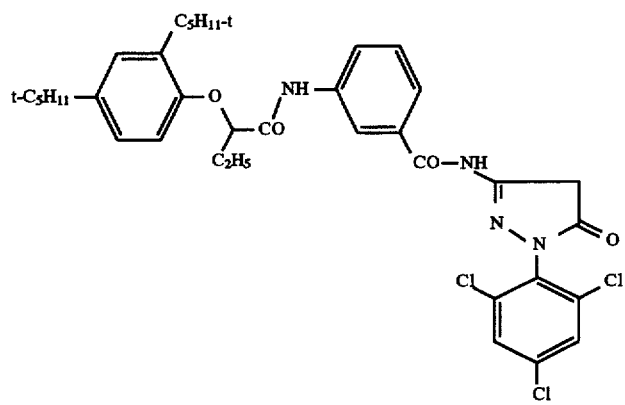
M-1
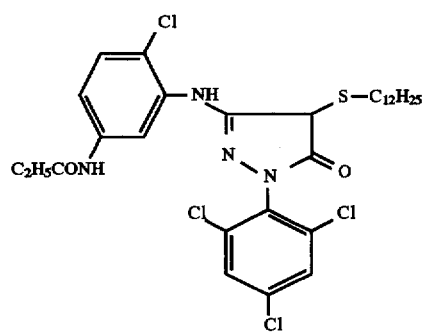
M-2
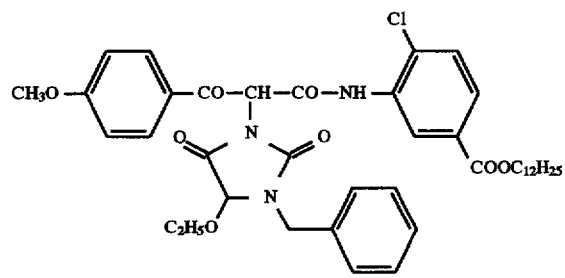
Y-1

CM-1
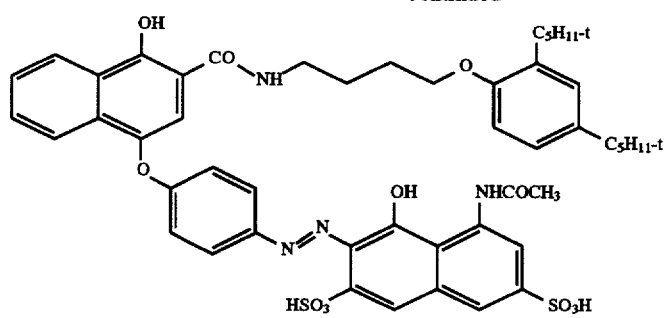
CY-1
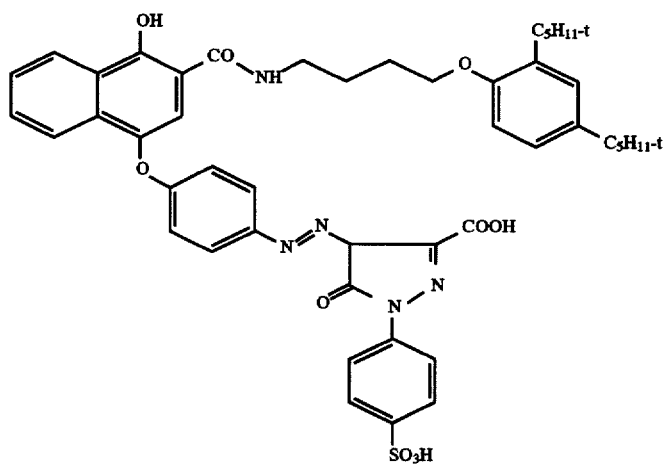
MY-1
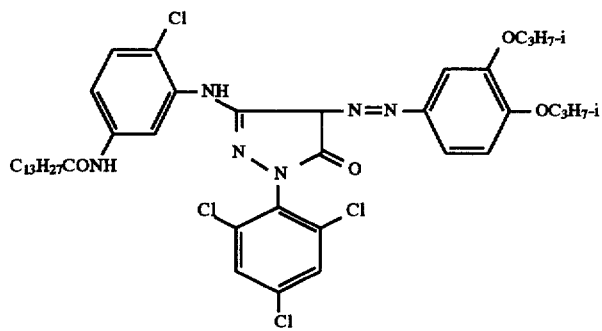
MY-2
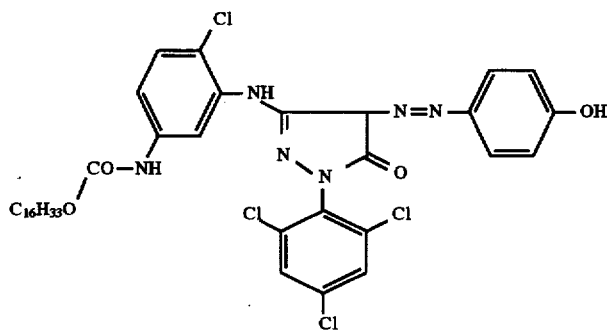

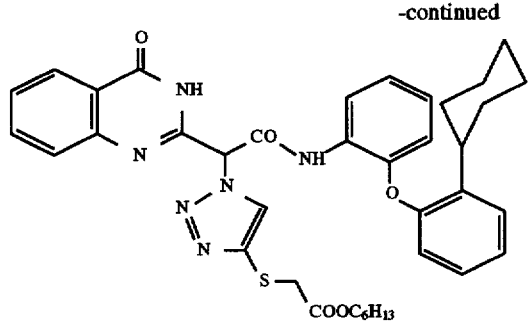
D-1
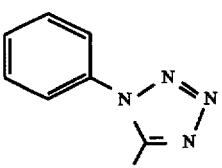
D-2
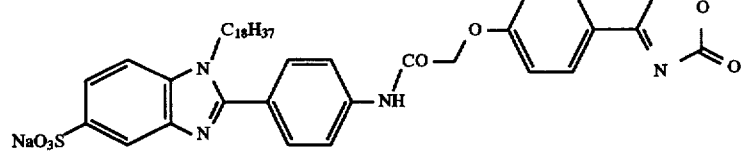
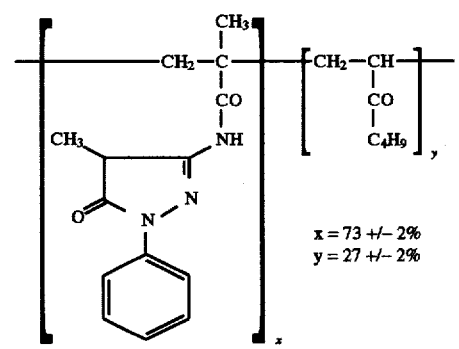
W-1
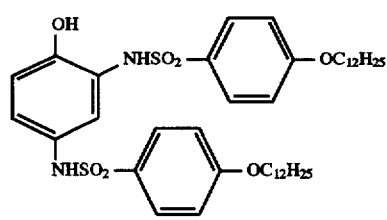
W-2
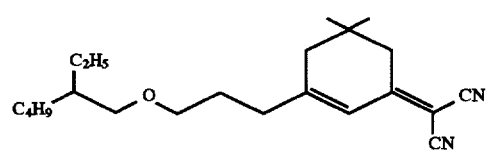
UV-1
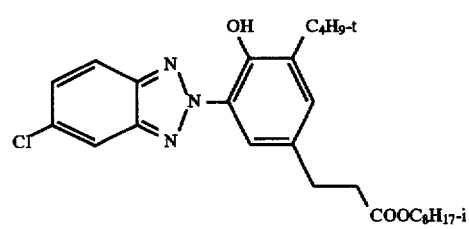
UV-2

[Structure: imidazolidine-2,4-dione with N-methyl, comparison compound A]

[Structure F-1: morpholine-N-carbonyl pyridinium with ethanesulfonate]

All the emulsions were stabilised with 0.034 mmole of comparison compound A per mole Ag, analogously to Example 1.

Example 2.2

This corresponds to Example 2.1, except that the emulsions were stabilised with 0.024 mmole of compound 1.

Four samples of the material from each of Examples 2.1 and 2.2 were tested as follows:

2.1.1 Exposure, storage for 7 days at 20° C. and 45% relative humidity
2.1.2 Exposure, storage for 7 days at 60° C. and 34% relative humidity
2.1.3 Exposure, storage for 7 days in a humid climate at 35° C. and 90% relative humidity
2.1.4 Storage for 7 days in a humid climate at 35° C. and 90% relative humidity, followed by exposure
2.2.1 as 2.1.1
2.2.2 as 2.1.2
2.2.3 as 2.1.3
2.2.4 as 2.1.4

The different materials were exposed to daylight behind a graduated wedge filter. Thereafter the materials were processed according to the process described in the British Journal of Photography 1974, page 597.

The following sensitivity values in DIN were determined for measurements behind blue, green and red filters (3 DIN units correspond to a doubling of sensitivity).

|       | Eyl  | Emg  | Ecy  |
|-------|------|------|------|
| 2.1.1 | 35.5 | 34.3 | 34.7 |
| 2.1.2 | 35.0 | 34.1 | 34.1 |
| 2.1.3 | 34.7 | 33.7 | 34.0 |
| 2.1.4 | 35.0 | 33.0 | 33.0 |
| 2.2.1 | 35.6 | 34.2 | 34.5 |
| 2.2.2 | 35.4 | 34.1 | 34.5 |
| 2.2.3 | 35.3 | 34.0 | 34.1 |
| 2.2.4 | 35.3 | 34.0 | 33.6 | yl = yellow; mg = magenta; cy = cyan

[Structure H-1]

The results show that stabilisation with an isoselenazolone stabiliser according to the invention leads to significantly lower losses of sensitivity, both exposed and unexposed, particularly under tropical storage conditions (compare 2.2.3 with 2.1.3 and 2.2.4 with 2.1.4, respectively).

Example 3.1 (comparison)

The following solutions were each made up with demineralised water:

Solution 1:
  7000 ml water
  540 ml gelatine

Solution 2:
  7000 ml water
  1300 g NaCl
  21.5 g KBr
  $5 \cdot 10^{-5}$ g $K_2IrCl_6$
  $3 \cdot 10^{-5}$ g $Na_3RhCl_6$
  $2 \cdot 10^{-6}$ g $HAuCl_4$
  $1.5 \cdot 10^{-4}$ g $PtCl_4$ Solution 3:
  7000 ml water
  3000 g $AgNO_3$ Solutions 2 and 3 were added simultaneously, at a pAg of 7.7 and with intensive stirring, to solution 1 at 50° C. over 120 minutes. A silver chloride emulsion with an average particle diameter of 0.8 μm was obtained. The gelatine/$AgNO_3$ weight ratio was 0.18. The emulsion was flocculated in the known manner, washed, and re-dispersed with an amount of gelatine such that the gelatine/$AgNO_3$ weight ratio was 1.0. The emulsion contained 1 mole of silver halide per kg. The emulsion was then optimally ripened at a pH of 4.5 with 3.5 μmole gold chloride/mole Ag and 1.5 μmole $Na_2S_2O_3$/mole Ag. After the chemical ripening the emulsion (silver halide composition: $AgCl_{0.99}Br_{0.01}$) was stabilised and sensitised for the blue spectral region.

Thereafter the emulsion was mixed with a solution of yellow coupler of formula

[Structure of yellow coupler with $(CH_3)_3$—CO—CH—CO—NH— group, pyrazole, and phenyl with $O—C_{16}—H_{33}$ and $SO_2—NH—CO—C_2H_5$ substituents]

and of white coupler of formula

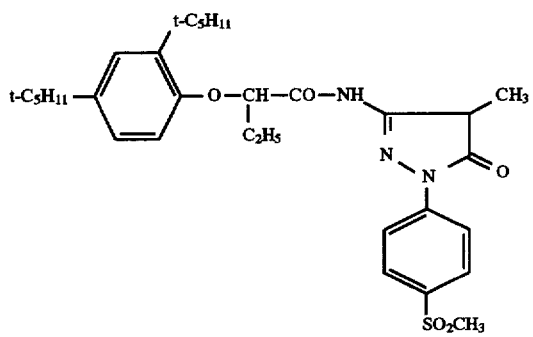

in tricresyl phosphate and deposited on a layer support comprising paper coated on both sides with polyethylene.

The layer contained (per m²):

0.63 g AgNO₃
1.38 g gelatine
0.95 g yellow coupler
0.2 g white coupler
0.29 g tricresyl phosphate.

A protective layer comprising (per m²) 0.2 g gelatine and 0.3 g of hardener of formula

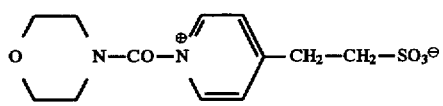

was cast over this layer.

Examples 3.2–3.6 (according to the invention)

Samples 3.2 to 3.6 differed from sample 1 in that the following additives were added to the emulsions before the addition of the emulsified preparation of yellow coupler:

3.2. 15 mg compound 1
(0.1 weight % methanolic solution)

3.3. 30 mg compound 1
(0.1 weight % methanolic solution)

3.4. 15 mg compound 1
50 mg compound A
(as an 0.1 weight % methanolic solution)

3.5. 15 mg compound 1
40 mg N-acetyl-L-cysteine
(as an 0.1 weight % methanolic solution)

3.6 15 mg compound 1 (as an 0.1 weight % methanolic solution)
50 mg glutathione as an 0.1 weight % aqueous solution.

Example 3.7 (comparison)

Sample 3.7 contained 30 mg compound A as an additive.

One sensitometer strip from each of the cast sample lengths was stored under deep-freeze conditions for 3 months, and a second strip from each sample length was stored for 3 months at 20° C. and 34% relative humidity.

The sample strips were then exposed behind a wedge filter and processed by the Ektacolor RA-4 process.

| | Sensitometric data | | | | |
|---|---|---|---|---|---|
| | Sample after storage under deep-freeze conditions (90 days; –18° C.) | | Sample after storage at room temperature (90 days) | | |
| | $D_{min}$ | log Lt | $D_{min}$ | log Lt | $\Delta D_{min}$ |
| 3.1. | 0.210 | 2.05 | 0.239 | 1.68 | +0.029 |
| 3.2. | 0.131 | 2.01 | 0.145 | 1.80 | +0.014 |
| 3.3. | 0.115 | 1.28 | 0.128 | 1.90 | +0.013 |
| 3.4. | 0.210 | 2.10 | 0.240 | 1.85 | +0.030 |
| 3.5. | 0.120 | 2.01 | 0.120 | 1.98 | ±0.0 |
| 3.6. | 0.115 | 2.00 | 0.119 | 1.95 | +0.04 |
| 3.7 | 0.220 | 2.10 | 0.250 | 1.80 | +0.030 |

The results illustrate both the fogging- and sensitivity-stabilising effect and the improvements which are obtained by the simultaneous use of isoselenazolone stabilisers according to the invention and amino acids containing SH groups.

The use of compound A alone (3.7.) is not capable of producing an effect which is adequate to eliminate fogging.

We claim:

1. A photographic silver halide material comprising at least one silver halide emulsion layer, wherein the at least one silver halide emulsion layer is stabilized with a compound of formulae (I) or (II)

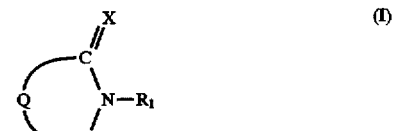

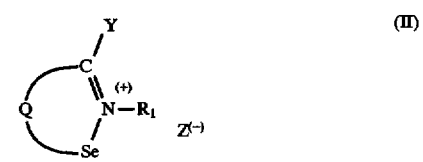

where
X represents O or NR₂
Y represents halogen,
Z⁻ represents an anion
R₁ represents hydrogen, alkyl, aryl, acyl or a heterocyclic group, or R₁ jointly with NR₂, represents remaining members of a condensed ring,
R₂ represents hydrogen, alkyl, aryl, acyl, or a heterocyclic group and
Q represents atoms required for completing a 5- or 6-membered ring.

2. The photographic silver halide material according to claim 1, wherein the at least one silver halide emulsion layer is stabilized with a compound of formula (III)

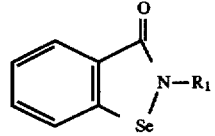

wherein R₁ represents hydrogen, alkyl, aryl, acyl or a heterocyclic group.

3. The photographic silver halide material according to claim 1, wherein the compound of formulae (I) or (II) is added to the silver halide emulsion to be stabilized in an amount of $10^{-7}$ to $10^{-3}$ mole/mole of silver halide.

4. The photographic silver halide material according to claim 1, wherein the silver halide emulsion of the at least one silver halide emulsion layer is a silver bromide-iodide or silver bromide-iodide-chloride emulsion with up to 15 mole % silver iodide and up to 30 mole % silver chloride.

5. The photographic silver halide material according to claim 1, wherein the silver halide emulsion of the at least one silver halide emulsion layer is a silver chloride emulsion with up to 20 mole % silver bromide and/or up to 10 mole % silver iodide.

6. The photographic silver halide material according to claim 1, wherein the silver halide emulsion of the at least one silver halide emulsion layer contains tabular silver halide grains with an aspect ratio of a least 3:1, which make up at least 50% of the projected area of the emulsion.

7. The photographic silver halide material according to claim 1, wherein the silver halide emulsion of the at least one silver halide emulsion layer contains a sulphur-containing amino acid as an additional stabilizing compound, in an amount of $10^{-7}$ to $10^{-3}$ mole/mole silver halide.

8. The photographic silver halide material as claimed in claim 1, wherein Y is chlorine, and $Z^{\ominus}$ is chloride.

9. The photographic silver halide material as claimed in claim 2, wherein $R_1$ is selected from the group consisting of phenyl, benzyl cyclohexyl, 2-fluorophenyl, 4-carboxyphenyl, 4-trifluoromethylphenyl, 4-(1-carboxyethyl)-phenyl, 4-dimethylaminophenyl, pyrimidinyl-(2), 3-hydroxypyridinyl-(2), 3,3-dioxo-3-thiacyclopentyl, tert.-butyl, ω-carboxy-n-pentyl, benzthiazolyl-(2), acetyl, 2-pyridyl-(4-)-ethyl hydrochloride, 2,2-dimethoxyethyl and hydrogen.

10. The photographic silver halide material as claimed in claim 1, wherein the compounds of formula I and formula II are selected from the group consisting of:

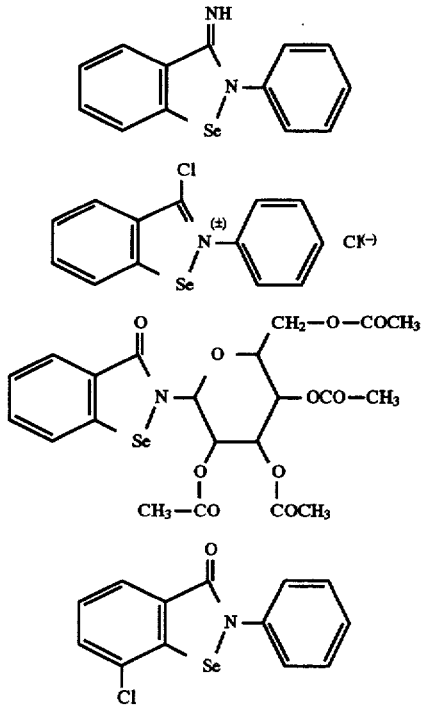

-continued

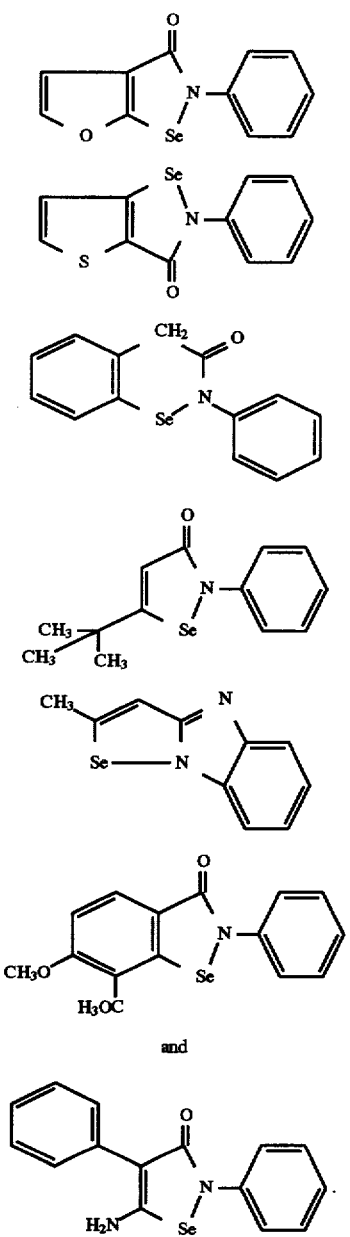

and

11. The photographic silver halide material as claimed in claim 4, wherein the silver halide emulsion layer is iodide-free and consists essentially of at least 95 mole % of silver chloride.

12. The photographic silver halide material according to claim 6, wherein the silver halide emulsion of at least one silver halide emulsion layer contains tabular silver halide grains with an aspect ratio of 5:1 to 25:1, which make up at least 70% of the projected area of the emulsion, and have a thickness less than 0.3 μm.

13. The photographic silver halide material according to claim 12, wherein the thickness is between 0.03 to 0.2 μm.

* * * * *